| United States Patent [19] | [11] Patent Number: 4,814,323 |
| Andrieu et al. | [45] Date of Patent: Mar. 21, 1989 |

[54] PROCESS FOR THE TREATMENT AND THE PREVENTION OF AIDS AND OTHER DISORDERS INDUCED BY THE LAV/HTLV III VIRUS

[76] Inventors: J. M. Andrieu, 7 Rue du Val de Grace; P. Even, 59 Rue Vaneau, both of 75007 Paris; Alain Venet, 5 MS Quoi de lo Rifubli, 94410 Saint Maurice, all of France

[21] Appl. No.: 843,563

[22] Filed: Mar. 25, 1986

[51] Int. Cl.⁴ .............................................. A61K 37/02
[52] U.S. Cl. ...................................... 514/11; 514/934; 514/885
[58] Field of Search ........................... 514/11, 934, 885

[56] References Cited

U.S. PATENT DOCUMENTS 4,288,431  9/1981  Traber et al. ...................... 514/11

OTHER PUBLICATIONS

*Basic and Clinical Immunology,* 5th ed., Lange Medical Publications, Los Altos, Calif., 1984, pp. 180, 415–417 and 420.

*Primary Examiner*—Delbert R. Phillips
*Assistant Examiner*—F. T. Moezie
*Attorney, Agent, or Firm*—Wegner & Bretschneider

[57] ABSTRACT

The invention relates to a process for the treatment and the prevention of the acquired immunodeficiency syndrome (AIDS) and AIDS related complex (ARC) induced by the LAV/HTLV III virus in a patient infected with said virus, comprising administering to said patient an effective amount of a compound selected from cyclosporins.

1 Claim, No Drawings

PROCESS FOR THE TREATMENT AND THE PREVENTION OF AIDS AND OTHER DISORDERS INDUCED BY THE LAV/HTLV III VIRUS

The present invention relates to a process for the treatment and the prevention of AIDS and other disorders induced by the LAV/HTLV III virus.

Only two years after the clinical emergence of the acquired immunodeficiency syndrome (AIDS) and the AIDS related complex (ARC), the discovery of the lentivirus responsible for these syndromes has enabled a decisive breakthrough in the knowledge of the disease, i.e. a viral destruction of the pivotal regulatory cell of the immune system, the T helper/inducer (T4) lymphocyte, leading to a progressive and irreversible immunodeficiency.

The AIDS virus (LAV or HTLV III) is an RNA exogeneously transmitted cytopathic non oncogenic lentivirus. The virus binds selectively to the T4 receptor of T4 cells, but cannot be propagated in vitro into monoctyes, T3, T8 and normal B lymphocytes. After entering the T4 cell, the viral RNA is retrotranscripted by a specific viral reverse-transcriptase into unintegrated linear DNA. The major part of the linear DNA is integrated into the cellular genome, each cell containing many copies inserted at random in chromosomal sites, variable from one cell to another (Shaw GM, et al, Molecular characterization of human T-cell leukemia (lymphotropic) virus type III in the acquired immune deficiency syndrome. Science 1984.226: 1165–71).

The natural evolution of the disease can be divided into an immunoactive period followed by an immunodepressed period.

1-The first immunoactive period is characterized by a number of clinical, histological and biological manifestations mimicking autoimmune diseases. This period may be clinically latent or expressed by a PGL, which is initially isolated or associated with systemic symptoms occurring generally after 1 to 3 years. During this period, many features are suggestive of an intensive immune response: (a) the outbreak of the disease, 2 to 4 weeks after the contamination by an influenza-like syndrome with fever, sore throat, macular rash, arthralgies and lymphadenopathy occuring simultaneously with the seroconversion and lasting a few weeks. This initial syndrome is frequently followed by the reappearance or the persistence for months or years of multiple, tender and fluctuating enlarged lymph nodes, specially in the cervical, occipital and axillary areas, with or without splenomagaly (PGL); (b) the explosive follicular hyperplasia of the cortex, paracortex and medullary zones of the lymph nodes with numerous large cleaved and non-cleaved cells, a high mitotic activity, a few plasmocytes and a patchy infiltration of both T4 and T8 cells in equal number; (c) the increase in spontaneous immunoglobulin secretion resulting from a polyclonal activation of B cells, similar to that observed after Herpes virus infections or in autoimmune diseases, such as systemic lupus erythrematous. It is responsible for the normal humoral response against the previously encountered antigens, the increased IgG, IgA and IgM levels, the presence of immune complexes, associated or not with autoimmune thrombopaenia or neutropaenia and more rarely with nephrotic or demyelinating syndromes, the high level of acid-labile α-interferon (IFN) and the low titres of so-called antinuclear antibodies somtimes observed. This polyclonal activation of B cells probably results partly form a T-independent stimulation of the B-cells by the AIDS virus or by the frequently associated herpes family viruses and partly from the lowering of a T4 inducer/suppressor cell subset.

2-The second period is that of an increasing immunodepression, resulting from the progressive and regular disappearance of the T4 cells. It begins with systemic symptoms, such as fever, extreme fatigability, weight loss and chronic diarrhea. Simultaneously, the PGL vanishes and the follicular hyperplasia gives place to follicular involution with hyalinisation, prominent angiogenesis and persistence of T8 cells, contrasting with a complete depletion of T4 lymphocytes. Sometimes, usually when the number of T4 cells is around 200–300/$\mu$l, a Kaposl's sarcoma or a B cell lymphoma develop, perhaps induced by lymphokines such as angiogenic factor or B cell growth factor. Finally, the opportunistic infections of full-blown AIDS occur a few months after the lymph node regression, usually when the T4 cells count has fallen in the range of 0–150/$\mu$l.

All immunostimulating or immunoadoptive treatments attempted up to now, natural and IFNs or IL2, thymic hormones and factors, transfer factor, so-called immunostimulating drugs, e.g. isoprinosine, azimexon, tuftsin, bestatin, cimetidine, thymic transplants and HLA matched lymphocyte transfusions or siblings or identical twin bone marrow transplants have completely failed, as underlined in two recent reviews (Gottlieb MS. et al, Immunotherapy of the acquired immune deficiency syndrome, In: Gallin JI, Fauci AS, eds. Advances in host defense mechanisms. New York: Raven Press, 1985; 5: 149–70, and Lotze MT. Treatment of immunologic disorders in AIDS. In De Vita VT, Hellman S, Rosenberg SA. eds. AIDS etiology, diagnosis, treatment, and prevention. New-York: Lippincott JB company, 1985: 235–63).

The present invention is based on a new therapeutic concept, viz the use of cyclosporins known as immunosuppressors.

Thus we have discovered that the administration of a compound selected from cyclosporins to a patient infected with the LAV/HTLV III virus and having a low number of T4 cells induces an increase of the T4 cell number up to a normal number or at least up to a subnormal number. In general this increase is accompanied by a disappearence of adenopathies and general symptoms at least in the patients at an early stage of the disease.

The administration of cyclosporins may be used for the prevention of AIDS in patients infected with the LAV/HTLV III virus before the appearance of the AIDS symptoms, that is patients with no symptoms or patients with ARC.

The administration of cyclosporins may also be used for the prevention of ARC in patients infected with the LAV/HTLV III virus before the appearence of ARC.

In the patients in which AIDS has appeared the administration of cyclosporins should at least induced a regression of the AIDS symptoms (such as Kaposi's Sarcoma) and the prevention of new opportunistic infections.

Thus the invention provides a process for the treatment and the prevention of the acquired immunodeficiency syndrome and other disorders induced by the LAV/HTLV III virus in a patient infected with said virus, comprising administering to said patient an effective amount of a compound selected from cyclosporins.

Among the cyclosporins, cyclosporin A is preferred. However cyclosporin G having low toxicity may also be used.

Cyclosporin A has been disclosed in U.S. Pat. No. 4,117,118 which is herein incorporated by reference. This patent discloses also a process for its production and its use as antibiotic and immunosuppressive agent.

Cyclosporins have never been suggested as useful in the treatment of AIDS. On the contrary it has been postulated that AIDS may be the result of the presence of an immunosuppressive cyclosporin-like molecule (see for example Schran et al Am J. Med. 1984, 775–797).

The cyclosporins may be administered by the parenteral and oral routes, and preferably by the intravenous route, typically by infusion or by the oral route.

By the intravenous route the daily dosage may be from 1 to 20 mg/kg, preferably from 3 to 10, and by the oral route from 1 to 50 mg/kg, preferably from 7 to 20 mg/kg.

The cyclosporins may be administered in association with a physiologically acceptable carrier or diluent. Such compositions conveniently contain more than 1% by weight of cyclosporins and may be prepared by conventional techniques to be in conventional forms, for example, capsules, tablets, suppositories, dispersible powders, syrups, elixirs, suspensions or solutions, for oral or parenteral administration. Suitable pharmaceutical diluents or carriers include, for example, water, alcohols, natural or hardened oils and waxes, calcium and sodium carbonates, calcium phosphate, kaolin, talc and lactose as well as suitable preserving agents, such as ethyl-hydroxybenzoate, suspending agents such as methyl cellulose, tragacanth and sodium alginate, wetting agents such as lecithin, polyoxyethylene stearate and polyoxyethylene sorbitan mono-oleate, granulating and disintegrating agents such as starch and alginic acid, binding agents such as starch, gelatin and acacia, and lubricating agents such as magnesium stearate, stearic acid and talc. Compositions in tablet form may be coated by conventional techniques to delay disintegration of the tablet and absorption of the active ingredient in the gastrointestinal tract and thereby provide sustained action over a long period. A preferred form is an injectable form comprising as carrier an isotonic solution. For the oral route the compositions may be under the form of a drinkable solution which may be diluted with milk.

Clinical trials with cyclosporin A (CsA)

A-Patients and methods

All patients responded to the definition of the Centers for Disease Control.

There were 4 AIDS patients, all male homosexual, 28 to 38 years old.

Patient A developed a Pneumocystis Carinii pneumonia (PCP) in December 1984, followed by two episodes of cerebral toxoplasmosis. These were treated by pyrimethamine and sulfadiazine which on both occasions led to severe neutropaenia and thrombopaenia. Throughout this period the T4 cell count never exceeded 100/µl. The patient was admitted in the department moribund and comatose. He was immediately treated with pyrimethamine, sulfadiazine and high dose steroid therapy. After 3 days, his condition improved and CsA was started.

Patient B had a past history of polycythaemia evolving towards myelosclerosis. He was admitted with a severe PCP which resolved in 4 days with a high dose of cotrimoxazole. CsA was started after 3 days of antiinfectious therapy.

Patient C had a persistent gneralized lymphadenopathy (PGL) since April 1984. He was admitted, severely cachectic and short of breath but without any more adenopathies. A diagnosis of severe PCP was established, necessitating mechanical ventilation. In spite of cotrimoxazole treatment, he died after 9 days. He received IV CsA only the last 2 days.

Patient D had a PGL for 3 years. A cutaneous Kaposi's Sarcoma developed in October 1985 and lymph nodes disappeared simultaneously.

There were 6 Non-AIDS patients, five males and one female, all having been contaminated by sexual contact. The mean age was 35±6 years. Patients 1–4 had PGL for 12 to 48 months. Patient 2 also had constitutional symptoms (CS). Patients 5 and 6 had neither PGL nor constitutional symptoms but fewer than 250 T4 cells/l.

All patients has an initial work-up including clinical evaluation, two controls of anti-LAV antibodies (HTLV III Abbott EIA) and blood cell counts, T subset lymphocyte counts, renal and hepatic functions analysis. T4, T6 and T8 peripheral blood cell counts were determined by indirect immunofluorescence with OKT4, OKT6 and OKT8 monoclonal antibodies (Ortho, Raritan, USA) and fluorescein-conjugated goat antimouse IgG (Dynatech, Paris, France) using a fluorescence microscope equipped with phase contrast optics (Olympus BHB, Tokyo, Japan). Informed consent was obtained from all conscious patients. CsA was started orally at a dose of 10 mg/kg/day or by IV route at a dose of 4 mg/kg/day in continuous infusion (unless otherwise stated). Estimation of plasma CsA levels were performed at 21° using a radioimmunoassay kit (Sandoz Ltd).

B-Results

The 6 Non-AIDS patients had an initial mean total lymphocyte (TL) count of 1500±640/µl and a mean T4 cell count of 410±160/µl (table I). The range of plasma CsA concentrations was 100–370 ng/ml on the 3rd–4th day of treatment. CsA dosage was subsequently adjusted to obtain a 120–250 ng/ml level. By the fourth-seventh day, the T4 cell (1290±235) and TL (3120±640) counts were normalized. This normalization has been maintained after 8 to 12 weeks. Simultaneously, the T8 cell count rose from 610±160 to 1500±450/µl. Lymphadenopathies (and constitutional symptoms) disappeared completely in patients 2, 3 and 4 and diminished markedly in patient 1. The initial T6 count, when initially performed, ranged from 70 to 200/µl, i.e. 8 to 15% of the TL. After 4–7 days of CsA, the T6 count reached 360–880/µl or 14–30% of the TL count. Although double labelling (T4, T6) has not yet been performed, it is likely that OKT4 and OKT6 monoclonal antiboides are bound to the same cells, because these cells have similar cytological patterns (enlarged size with increased cytoplasm) whereas the OKT8 labelled cells are small cells with their usual cytological features.

In AIDS patient A (table II), the TL count and the various T cell subsets had a rapid initial increase. After 5 days of CsA (10 mg/kg PO), the T4 cells increased by a factor 100 and the T6 cells reached around 20% of the TL. From the same day, diarrhea occurred and the CsA plasma level fell under 35 ng/ml with the result that T4 and TL rapidly decreased. CsA was changed to IV continuous route (4 mg/kg), which entailed a reincrease of T4 and TL counts. From the 10th day, a progressive pancytopaenia with a rapid lowering of platelets, neutrophils and lymphocytes occurred. Sulfadiazine, which had previously provoked such a pancytopaenia twice, was then stopped. CsA was also stopped. Nevertheless, pancytopaenia continued and the patient died on the 18th day.

In AIDS patient B with myelosclerosis (table III), CsA (5 mg/kg IV) was started 3 days after the onset of cotrimoxazole therapy. A progressive neutropaenia, which occurred from the 5th day, suggested a cotrimoxazole-induced myelotoxicity. Simultaneously, the creatinine level rose to 210 μm/l and the CsA plasma level was 300 ng/ml. CsA dosage was then dropped to 2.8 mg/kg and since the respiratory condition of the patient had become normal, cotrimoxazole was stopped on the 7th day. T4 and TL counts then showed a moderate increase followed by a return to previous values.

AIDS patient C received CsA (3 mg/kg IV) the last two days of his life only, which entailed an increase from 60 to 210 T4 cells/μl.

AIDS patient D had no change in his T4 and TL counts over a 10-day period. His CsA plasma level was 120 ng/ml on the 8th day.

TABLE I

Total lymphocyte (TL) counts and T cell subsets (cells/μl) in Non-AIDS patients before and during treatment with Cyclosporine A

| Patient Number | Before | Day 4 | Day 7 | Day 14 | Day 28 |
|---|---|---|---|---|---|
| | | | T4/TL; (T4 percentage) T8/T6 | | |
| 1 | 580/1020; (57) 390 | | | 850/1930; (41) 790/580 | 1035/2160; (48) 840/216 |
| 2 | 305/1380; (22) 800/200 | | 980/2960; (33) 2070/240 | 990/2960; (33) 2070/440 | |
| 3 | 590/2680; (22) | 1560/4000; (39) 1840 | 1530/3560; (43) 1790/890 | 1620/4370; (37) | 1010/3170; (32) 1460 |
| 4 | 485/1430; (34) 590 | 1310/3190; (41) 1630/765 | | 980/2170; (45) 740/960 | |
| 5 | 240/1620; (15) 745/130 | 1295/2695; (48) 1430/675 | | | |
| 6 | 240/875; (27) 470/70 | 985/2595; (38) 1170/360 | | | |

TABLE II

| | AIDS patient A. | | | | | |
|---|---|---|---|---|---|---|
| DAYS | 1 | 5 | 9 | 10 | 13 | 17 |
| Platelets × 10³/μl | 50 | 115 | 70 | 60 | 30 | 5 |
| Neutrophils/μl | 2,900 | 2,100 | 2,100 | 2,200 | 1500 | 500 |
| Lymphocytes/μl | 370 | 1,020 | 470 | 870 | 300 | 300 |
| T4/μl (percent) | 4(1) | 330(33) | 70(15) | 220(25) | 10(3) | 40(13) |
| T8, T6/μl | 100, — | 400, 160 | 300, 105 | 530, 180 | —, 35 | — — |
| CsA, mg/kg | Start, 5 | 10 (oral) | 10 (oral) | 4 (IV) | 4 (IV) | 0 |
| Plasma CsA, ng/ml | — | — | 30 (diarrhea) | — | 415 | — |

TABLE III

| | AIDS patient B. | | | |
|---|---|---|---|---|
| DAYS | 1 | 5 | 7 | 9 |
| Platelets × 10³/μl | 130 | 145 | 160 | 200 |
| Neutrophils/μl | 4,000 | 1,800 | 2,500 | 1,600 |
| Lymphocytes/μl | 600 | 570 | 1190 | 650 |
| T4/μl (percent) | 180 (30) | 170 (30) | 380 (32) | 235 (36) |
| T8, T6/μl | 340, 40 | 250, 180 | 590, 380 | —, 160 |
| CsA, mg/kg (IV) | Start, 5 | 5 IV | 2,8 IV | 2,8 IV |
| Plasma CsA, ng/ml | — | 300 | — | — |
| Creatinine μm/l | 90 | 210 | 160 | 150 |

We claim:

1. Process for increasing the T4 cell number in a patient infected with LAV/HTLV III virus, comprising administering an effective amount of cyclosporin A.

* * * * *